Jan. 17, 1967 E. H. MILLER Plant Pat. 2,699
CHRYSANTHEMUM PLANT
Filed Nov. 18, 1965
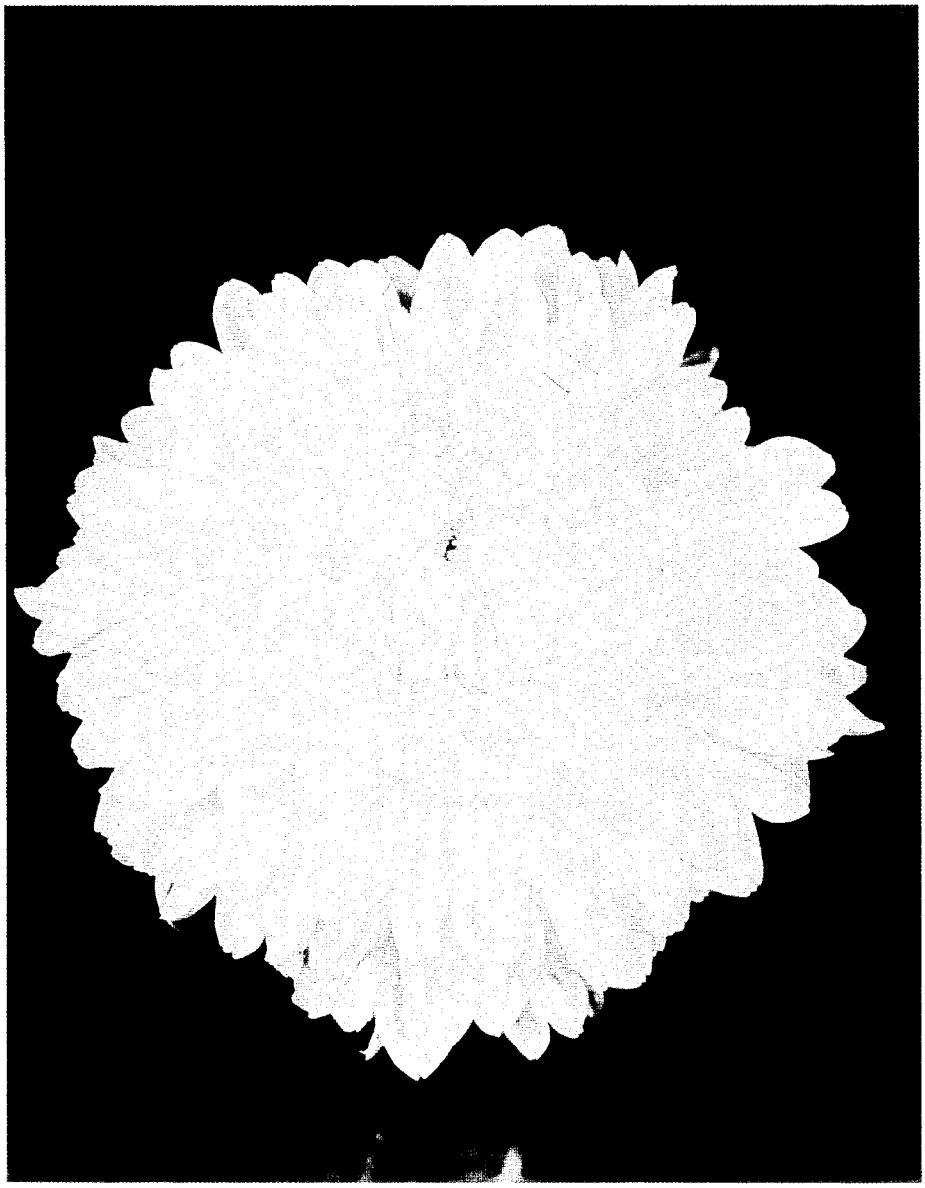
Inventor
Edward Miller
by Robb & Robb
attorneys United States Patent Office Plant Pat. 2,699
Patented Jan. 17, 1967

2,699
CHRYSANTHEMUM PLANT

Edward H. Miller, Mount Vernon, Ohio, assignor to Orville O. Dunham, Niles, Mich.

Filed Nov. 18, 1965, Ser. No. 508,608
1 Claim. (Cl. Plt.—77)

My present discovery comprises a new and distinct variety of chrysanthemum plant which is a sport of the variety disclosed in Plant Patent No. 2,001 and as such comprises another so-called white variety of the giant chrysanthemum class, retaining the early flowering characteristics of the parent plant and the short compact growth habit thereof.

This giant chrysanthemum class to which reference has been made previously, is a class of mums wherein the blooms are in the area of 6" in diameter or larger, and some of the varieties are found on short strong stems whereas others are grown on long stems.

The short compact type of plant is more desirable from many aspects since it lends itself to greenhouse use for spring flowering pots.

The particular variety of my discovery, is characterized by the Primrose Yellow center to creamy white general tonality of its blooms when viewed from a distance, together with the earliness and large size of the blooms, and the short compact vigorous growth habit which has continuously been produced in reproduction of the instant variety.

The plant itself grows to a height of 15" on the average, and is in contrast therefore to the much taller varieties disclosed in Plant Patents 2,005 and 2,007.

My new variety has been asexually reproduced by cuttings in the vicinity of Mount Vernon, Ohio, and as previously pointed out, is a white sport of a parent Plant Patent 2,001 which in itself is a strong pink to deep pink as indicated by comparison with the Nickerson Color Fan published by the Munsel Color Company.

The instant variety is compared with the Royal Horticultural Colour Chart and the fact that it is of white series so-called is an interesting distinction over said parent variety.

My new variety when grown in the vicinity of West Chicago, Illinois, blooms from early September until a killing frost, the observations from which this description is prepared having been made in a greenhouse in the vicinity of West Chicago, Illinois.

My new variety has been found to retain its distinctive characteristics through successive asexual reproduction.

My new variety may be compared with other known varieties, as previously mentioned, the varieties of Plant Patents 2,005 and 2,007, which are white giant chrysanthemums likewise, these previous varieties having been purposely hybridized from prior unpatented varieties, both whites in those instances, although the early flowering and growth habit are quite similar in all three instances, namely the prior patented varieties of Plant Patents 2,005, 2,007 and my discovery.

The accompanying drawing forming a part hereof shows a typical bloom of my new variety, the colors being as nearly representative of the actual color of the blooms as is possible.

The following is a detailed description of my new variety of chrysanthemum plant, the color references being to the Royal Horticultural Colour Chart:

*Description*

Parentage: Sport of the variety of Plant Patent No. 2,001.
Classification: Botanic—*Chrysanthemum indicum.*

*Flower*

Blooming habit: Blooms from early or mid-September profusely until a killing frost.

Bud:
- *Size.*—Large.
- *Form.*—Globular. Not affected by normal periods of hot or wet weather.

Color:
- *When sepals first divide.*—Chartreuse Green 663/2.
- *When petals begin to unfurl.*—Primrose Yellow 601/3.
- *When half blown.*—Inside of petals—Sulfur Yellow 1/3. Reverse of petals—Canary Yellow 2/3.
- *Sepals.*—Smooth edge.
- *Calyx.*—Shape—funnel. Size—large and slender. Aspect—smooth.
- *Peduncle.*—Length — medium. Aspect — smooth. Strength—stiff and heavy. Bud opens well.

Bloom:
- *Size.*—Large.
- *Average size when fully expanded.*—About 6" in diameter.
- *Borne.*—In clusters.
- *Stems.*—Medium and strong.
- *Form.*—Flat when first open.
- *Permanence.*—Retains its form to the end.
- *Petalage.*—Very double with innumerable petals under normal conditions.

Color:
- *Center of flower.*—Primrose Yellow 601/2.
- *Outer petals.*—Mimosa Yellow 602/3.
- *Base of petals.*—Mimosa Yellow 602/1.
- *Inside of petals.*—Mimosa Yellow 602/3.
- *Reverse of petals.*—Mimosa Yellow 602/3.
- *General tonality from a distance.*—Creamy white.
- *Discoloration.*—Retains the same general tonality through the third week.

Petals:
- *Texture.*—Thick. Long continuous periods of wet weather will rot the flower although it is not affected by hot weather.
- *Appearance.*—Inside—satiny. Outside—shiny.
- *Form.*—Pointed.
- *Arrangement.*—Imbricated.
- *Petaloids in center.*—Many.
- *Persistence.*—Hang on and dry.
- *Fragrance.*—None.

Genital organs:
- *Stamens, anthers.*—Small and many.
- *Arrangement.*—Regular around styles.
- *Stamens, filaments.*—Medium.
- *Styles.*—Columnar and even.
- *Length.*—Medium and thin.
- *Ovaries.*—Some protruding from calyx.

Plant:
- *Form.*—Bush.
- *Growth.*—Medium and compact.
- *Height.*—Average 15".
- *Spread.*—About 12".

Foliage:

*Size.*—Medium.
*Quantity.*—Normal.
*Shape.*—Lobed.
*Texture.*—Leathery.
*Ribs and veins.*—Prominent.
*Edge.*—Serrate.
*Serration.*—Single, large and deep.
*Under side.*—Rough.
*Stipules.*—Medium.

I claim:

A new and distinct variety of chrysanthemum plant, substantially as herein disclosed, characterized as to novelty by the Primrose Yellow center to creamy white general tonality of its blooms from a distance, the earliness and large size of its blooms, and its short, compact, vigorous growth habit.

No references cited.

ABRAHAM G. STONE, *Primary Examiner.*

R. E. BAGWILL, *Assistant Examiner.*